United States Patent
Sung et al.

(10) Patent No.: US 12,213,804 B2
(45) Date of Patent: Feb. 4, 2025

(54) EARBUD WITH TEMPERATURE SENSING

(71) Applicant: PIXART IMAGING INC., Hsin-Chu (TW)

(72) Inventors: Wei-Lun Sung, Hsin-Chu (TW); Po-Wei Yu, Hsin-Chu (TW); Chih-Ming Sun, Hsin-Chu (TW)

(73) Assignee: PIXART IMAGING INC., Hsin-Chu (TW)

( * ) Notice: Subject to any disclaimer, the term of this patent is extended or adjusted under 35 U.S.C. 154(b) by 172 days.

(21) Appl. No.: 17/849,941

(22) Filed: Jun. 27, 2022

(65) Prior Publication Data
US 2023/0414174 A1    Dec. 28, 2023

(51) Int. Cl.
*H04R 1/10* (2006.01)
*A61B 5/00* (2006.01)
*A61B 5/01* (2006.01)

(52) U.S. Cl.
CPC .......... *A61B 5/6817* (2013.01); *A61B 5/0008* (2013.01); *A61B 5/01* (2013.01); *H04R 1/1016* (2013.01); *A61B 2562/04* (2013.01)

(58) Field of Classification Search
None
See application file for complete search history.

(56) References Cited

U.S. PATENT DOCUMENTS

| | | | |
|---|---|---|---|
| 2015/0215719 A1* | 7/2015 | Turgul | H04R 1/1091 381/58 |
| 2016/0282187 A1* | 9/2016 | Sun | G01J 5/045 |
| 2019/0117155 A1* | 4/2019 | Cross | H04R 25/652 |
| 2021/0014598 A1* | 1/2021 | Pine | H04R 1/1041 |

FOREIGN PATENT DOCUMENTS

EP    3731536 A1 * 10/2020 ............... H04R 1/10

* cited by examiner

*Primary Examiner* — James K Mooney
(74) *Attorney, Agent, or Firm* — Li & Cai Intellectual Property (USA) Office (57) ABSTRACT

An earbud with temperature sensing is provided, and the earbud includes a housing, a speaker and a first temperature sensor. The housing defines a first opening and a second opening. The speaker is disposed within the housing and oriented so that audio emitted by the speaker exits the housing through the first opening defined by the housing. The first temperature sensor is positioned along an interior surface of the housing and aligned with the second opening in the housing for non-contact temperature sensing. In response to the earbud being positioned for use within an ear of a user, the second opening aligns with an inner side of the tragus close to the ear canal, the cavum conchae, an inner edge of the antitragus, or the cheek close to the ear, such that the first temperature sensor detects a body temperature of the user through the second opening.

14 Claims, 12 Drawing Sheets

EARBUD WITH TEMPERATURE SENSING

FIELD OF THE DISCLOSURE

The present disclosure relates to an earbud, and more particularly to an earbud with temperature sensing.

BACKGROUND OF THE DISCLOSURE

Wearable health devices are increasingly integrating a broad variety of sensors to better monitor heath status of users, and skin temperature is one of the vital signs for patient's health.

However, in the existing densely packaged earbuds, since sound components have taken up most of the space, it is difficult to provide a temperature sensor for parts where it is easy to measure the core temperature of a human body, such as the ear canal and the eardrum of the ear.

SUMMARY OF THE DISCLOSURE

In response to the above-referenced technical inadequacies, the present disclosure provides an earbud with temperature sensing.

In one aspect, the present disclosure provides an earbud with temperature sensing, and the earbud includes a housing, a speaker and a first temperature sensor. The housing defines a first opening and a second opening. The speaker is disposed within the housing and oriented so that audio emitted by the speaker exits the housing through the first opening defined by the housing. The first temperature sensor is positioned along an interior surface of the housing and aligned with the second opening in the housing for non-contact temperature sensing. In response to the earbud being positioned for use within an ear of a user, the second opening aligns with an inner side of the tragus close to the ear canal, the cavum conchae, an inner edge of the antitragus, or the cheek close to the ear, such that the first temperature sensor detects a body temperature of the user through the second opening.

Therefore, in the earbud with temperature sensing provided by the present disclosure, one or more openings can be arranged to align with one or more of an inner side of the tragus close to the ear canal, the cavum conchae, an inner edge of the antitragus, or the cheek close to the ear, such that the temperature sensor can detect a body temperature of the user through the one or more openings with good airtightness and high accuracy, while reserving sufficient space for integrating the components in the earphone without being affected by the sound components.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 1:
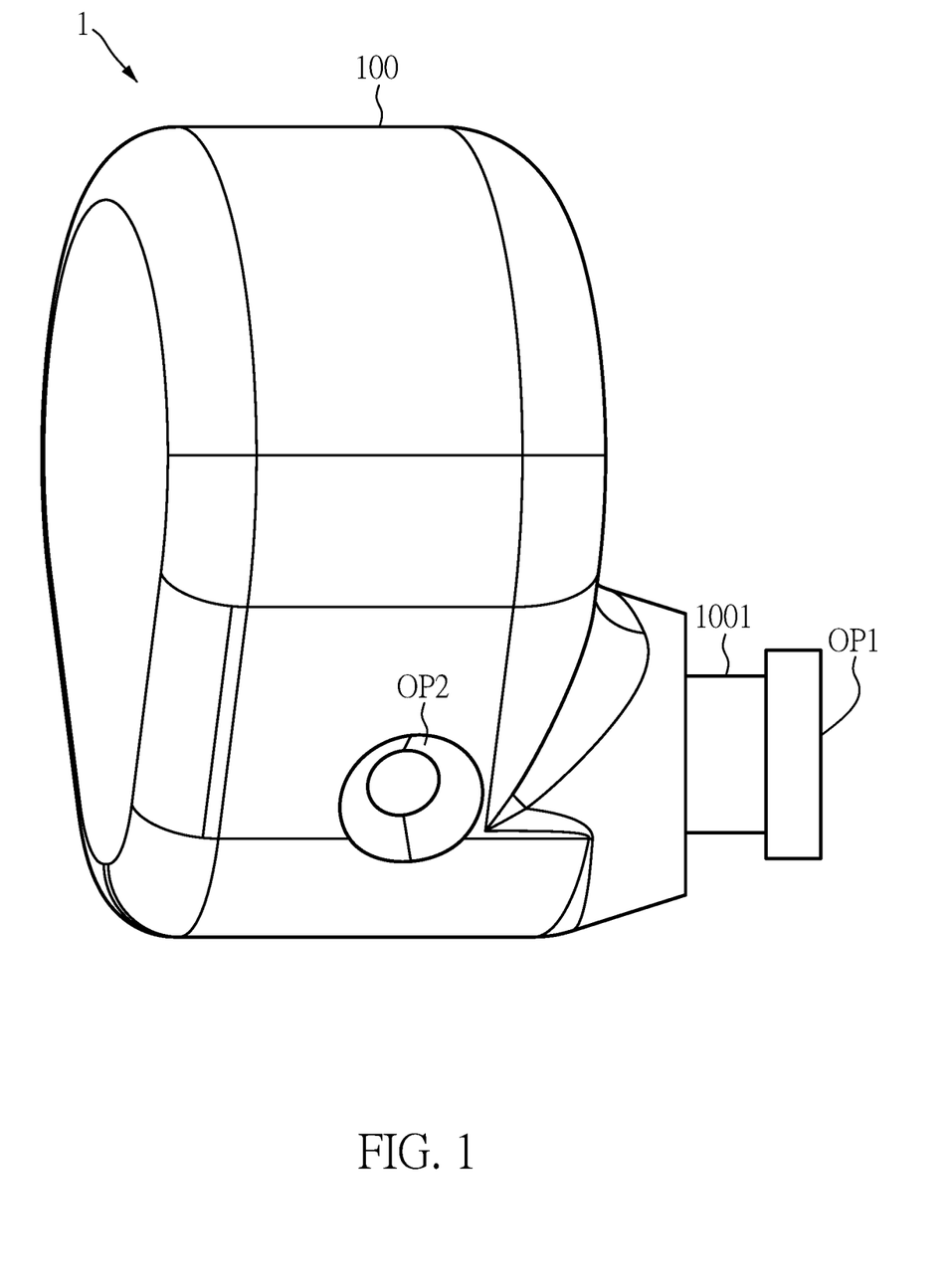
FIG. 1 shows a schematic side view of an earbud according to one embodiment of the present disclosure.
Figure 2:
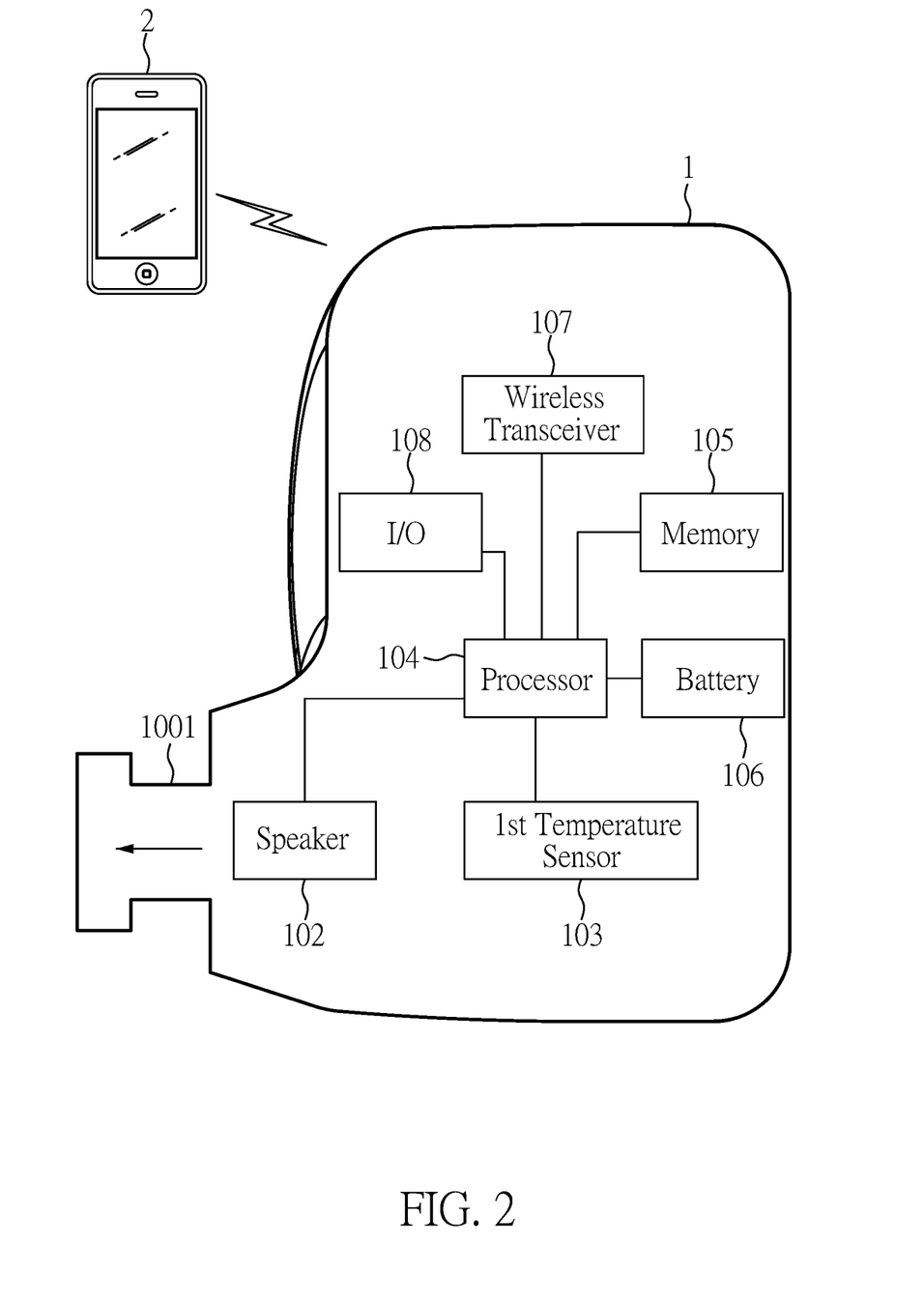
FIG. 2 is a functional block diagram schematically shown in a cross-sectional view of an earbud according to one embodiment of the present disclosure.
Figure 3:
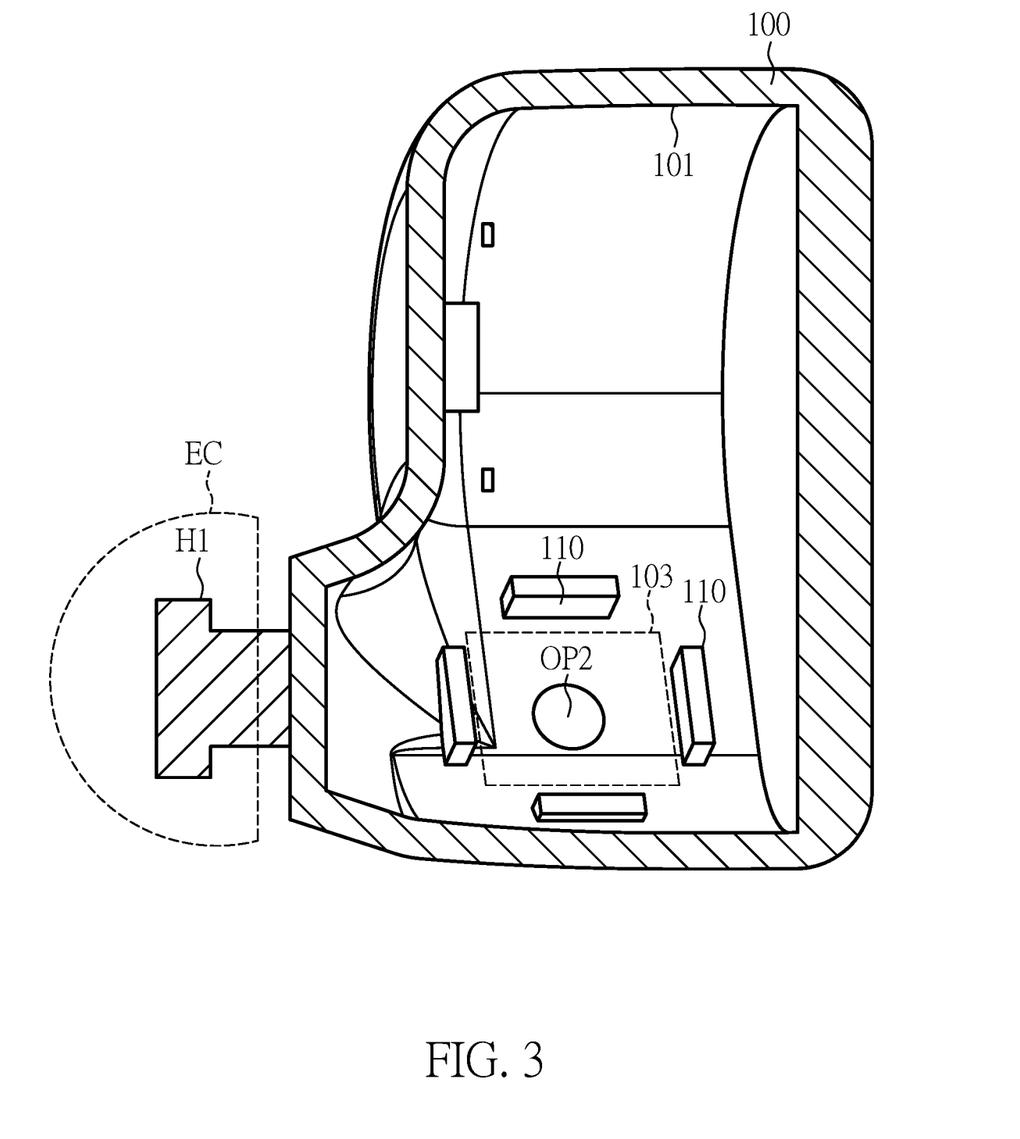
FIG. 3 is a cross-sectional view of an earbud according to one embodiment of the present disclosure.

FIG. 1 shows a schematic side view of an earbud according to one embodiment of the present disclosure, FIG. 2 is a functional block diagram schematically shown in a cross-sectional view of an earbud according to one embodiment of the present disclosure, and FIG. 3 is a cross-sectional view of an earbud according to one embodiment of the present disclosure. Referring to FIGS. 1-3, an earbud 1 includes a housing 100, a speaker 102 and a first temperature sensor 103. The housing 100 defines a first opening OP1 and a second opening OP2.

The speaker 102 can be disposed within the housing 100 and oriented so that audio emitted by the speaker 102 exits the housing 100 through the first opening OP1 defined by the housing 100. Specifically, the housing 100 can include a first protrusion 1001 with the first opening OP1 at a distal end of the first protrusion 1000. Moreover, as shown in FIG. 3, an ear cap EC made of elastomeric materials can be further pivotally coupled to the distal end of the first protrusion 1001 by a hinge H1.

As shown in FIG. 2, the earbud 1 further includes a processor 104, a memory 105, a battery 106, a wireless transceiver 107 and an input/output (I/O) interface 108. The processor 104 can be disposed within the housing 100 and configured to receive sensor data from the first temperature sensor 103.

As shown in FIG. 3, the first temperature sensor 104 can be positioned along an interior surface 1001 of the housing 100 and aligned with the second opening OP2 in the housing 100 for non-contact temperature sensing.

Furthermore, the first temperature sensor 103 can be, for example, a thermopile sensor, but the present disclosure is not limited thereto. The first temperature sensor 103 can be in electrical communication with the processor 104, which is responsible for controlling various aspects of earbud 1. For example, the processor 104 can gather the sensor data recorded by the first temperature sensor 103 and configured to transmit the sensor data to another device such as, for example, portable media device 2 by using the wireless transceiver 107 or the I/O interface 108 disposed in the housing 100. For example, the wireless transceiver 107 or the I/O interface 108 can be configured to provide a conduit for transmitting the sensor data provided by first temperature sensor 103, and can also be used to receive audio content that can be processed by the processor 104 and sent on to speaker 102.

In some embodiments, the wireless transceiver 107 or the I/O interface 108 can also receive control signals from a device similar to portable media device 2 for accomplishing tasks such as adjusting a volume output of speaker 102 or modifying a sensitivity, priority or duty cycle of the first temperature sensor 103. The wireless transceiver 107 can include an antenna configured to transmit and receive signals through an antenna window or an opening defined by the housing 100. This can be particularly important when the housing 100 is formed of radio opaque material. In some embodiments, the I/O interface 108 can also represent one or more exterior controls (e.g. buttons and/or switches) for performing tasks such as pairing the earbud 1 with another device or adjusting various settings of the earbud 1 such as volume or the like.

In other embodiments, the I/O interface 108 can be a wired interface that can provide power to the earbud 1 from another device or power source, and the battery 106 disposed within the housing 100 can be used for powering operations of the earbud 1. For example, the battery 106 can provide the energy needed to perform any of a number of tasks, such as maintain a wireless link, powering the processor 104, driving the speaker 102, powering the first temperature sensor 103, powering the wireless transceiver 107, and powering other components of the earbud 1 depicted hereinafter.

Furthermore, the earbud 1 can include a plurality of sensor positioning pins 110 positioned along the interior surface 101 of the housing 100 and around the second opening OP2 in the housing 100, such that the first temperature sensor 103 can align with the second opening OP2 by engaging the plurality of sensor positioning pins 110.

Figure 4:
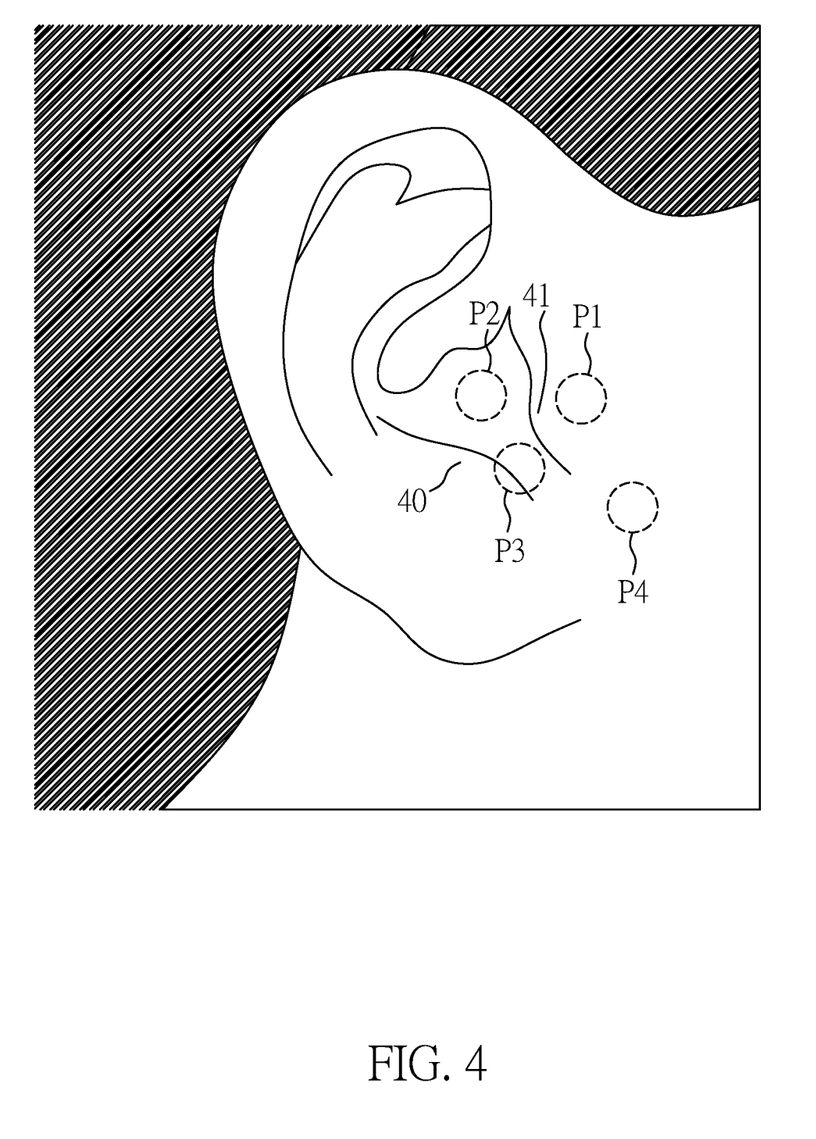
FIG. 4 is a schematic diagram showing possible positions that the first opening aligns with respect to a user's ear according to one embodiment of the present disclosure.

FIG. 4 is a schematic diagram showing possible positions that the first opening aligns with respect to a user's ear according to one embodiment of the present disclosure. Referring to FIG. 4, when the earbud 1 is positioned for use within an ear of a user, the second opening OP2 can align with positions P1, P2, P3 or P4. The position P1 corresponds to an inner side of the tragus 41 close to the ear canal, the position P2 corresponds to the cavum conchae, the position P3 correspond to an inner edge of the antitragus 40, and the position P4 corresponding to the cheek close to the ear. Therefore, the first temperature sensor 103 can be configured to detect a body temperature of the user through the second opening OP2.

Figure 5A:
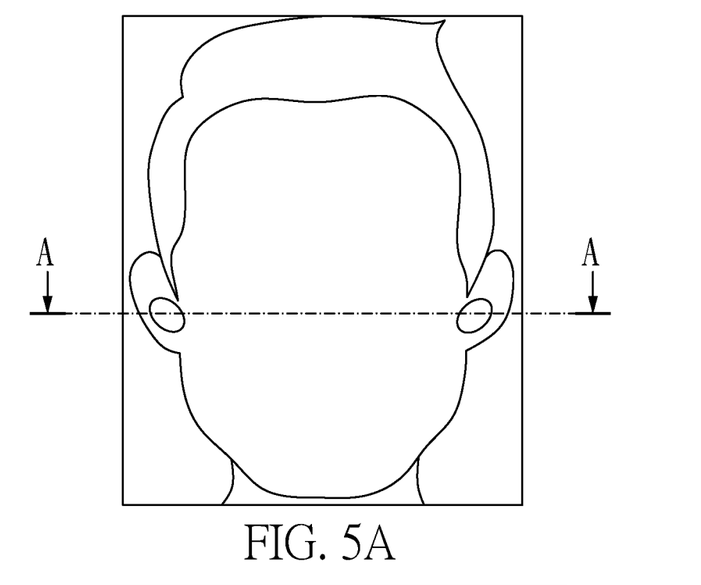
FIG. 5A is a schematic front view of a user wearing an earbud provided by the present disclosure.
Figure 5B:
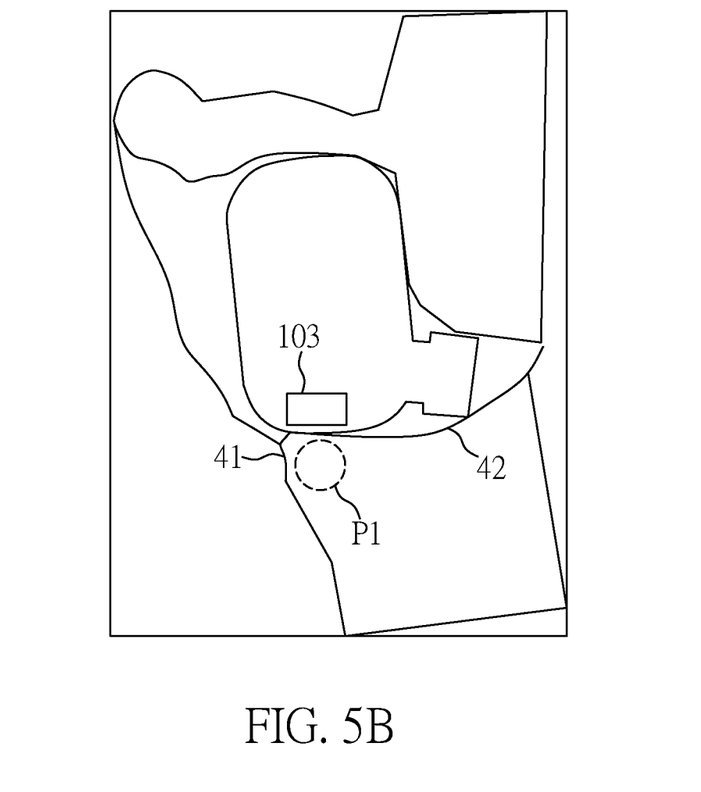
FIG. 5B is a schematic cross-sectional view taken along line A-A of FIG. 5A.

Reference can be further made to FIGS. 5A and 5B. FIG. 5A is a schematic front view of a user wearing an earbud provided by the present disclosure, and FIG. 5B is a schematic cross-sectional view taken along line A-A of FIG. 5A. As shown in FIG. 5B, when the earbud being positioned for use within the ear of the user, the second opening OP2 aligns with the inner side of the tragus 41 close to the ear canal 42, such that the first temperature sensor 103 detects a body temperature from the inner side of the tragus 41 close to the ear canal 42 of the user through the second opening OP2. When measuring the body temperature through the position P1, due to the good airtightness of this position, the obtained sensor data is not easily affected by the environment. In addition, since the position P1 is close to the blood vessel, the body temperature can be estimated more accurately.

It should be note that, when the processor 104 processes the sensor data and determines that the obtained body temperature is in a range of a human body temperature, the processor can further determine from the sensor data that whether the earbud is inserted in the user's ear.

Figure 6:
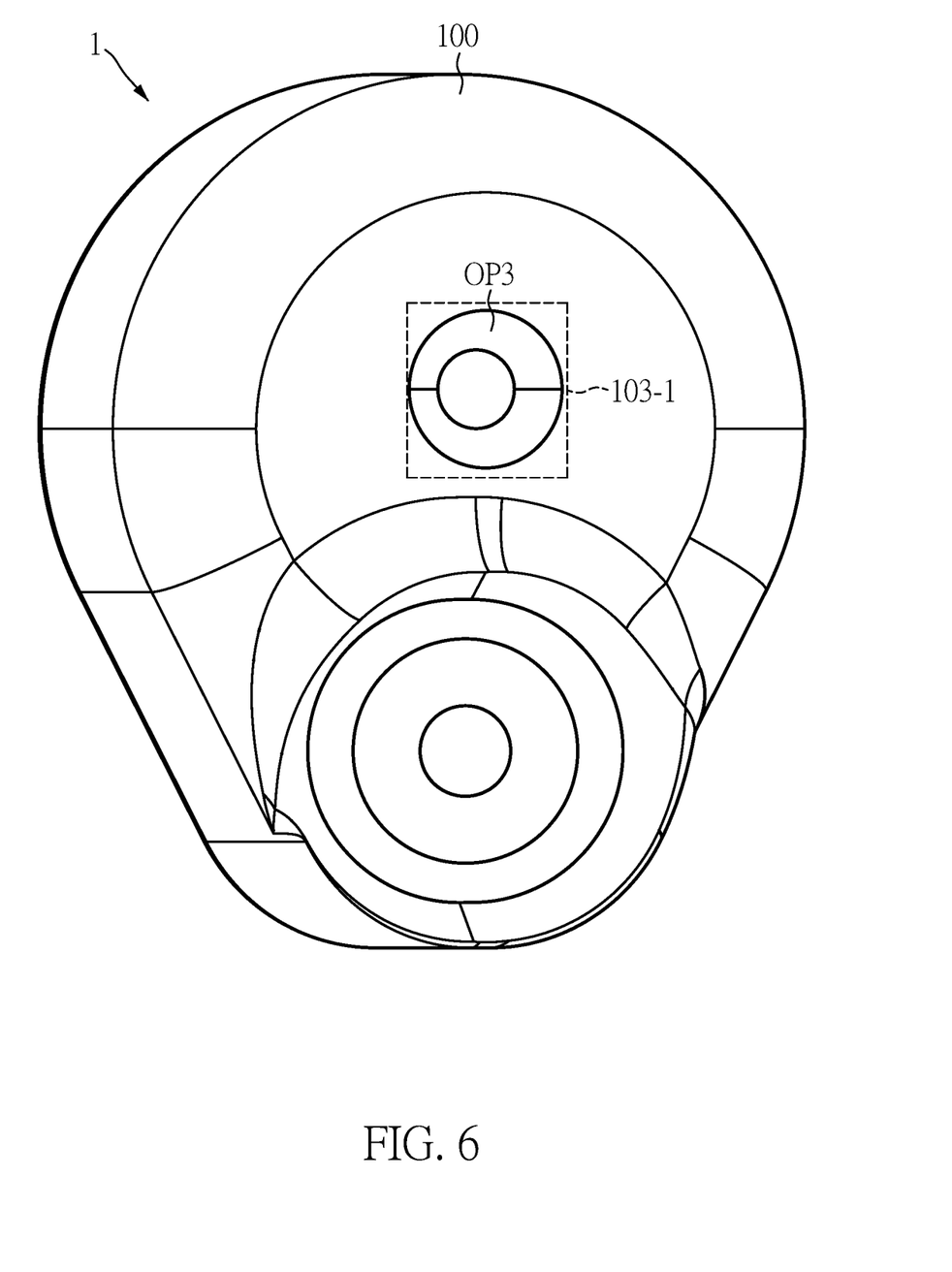
FIG. 6 shows another schematic side view of an earbud according to one embodiment of the present disclosure.

Referring to FIG. 6, FIG. 6 shows another schematic side view of an earbud according to one embodiment of the present disclosure. In the earbud 1 of FIG. 6, the housing 100 further defines a third opening OP3. In this case, the first temperature sensor 103 can be positioned to align the third opening OP3, or the earbud 1 can further include a second temperature sensor 103-1 positioned along the interior surface 101 of the housing 100 and aligned with the third opening OP3 for non-contact temperature sensing.

Figure 7A:
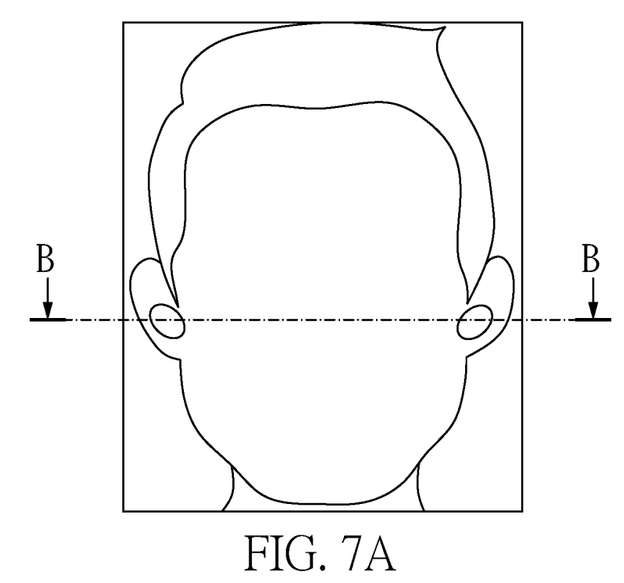
FIG. 7A is a schematic front view of a user wearing an earbud provided by the present disclosure.
Figure 7B:
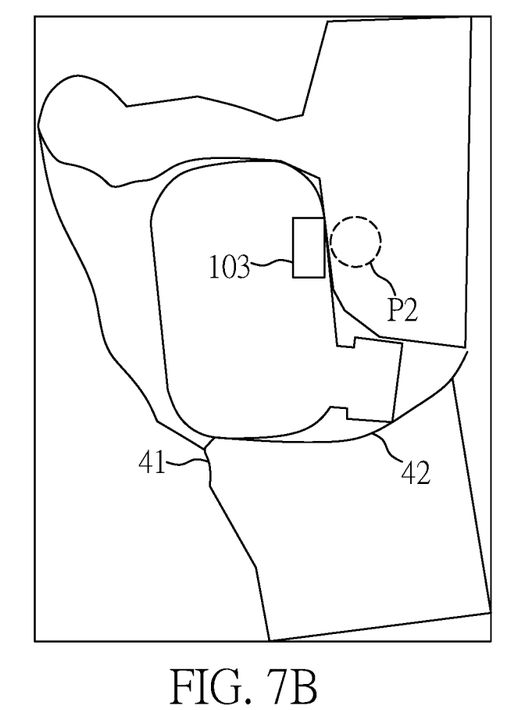
FIG. 7B is a schematic cross-sectional view taken along line B-B of FIG. 7A.

Reference can be further made to FIGS. 7A and 7B. FIG. 7A is a schematic front view of a user wearing an earbud provided by the present disclosure, and FIG. 7B is a schematic cross-sectional view taken along line B-B of FIG. 7A. As shown in FIG. 7B, when the earbud 1 being positioned for use within the ear of the user, the third opening OP3 aligns with the cavum conchae, such that the second temperature sensor 103-1 detects a body temperature from the cavum conchae (i.e., the position P2) of the user through the third opening OP3. When measuring the body temperature through the position P2, due to the good airtightness of this position, the sensor data is not easily affected by the environment. In addition, since the appearance consistency of each person in this position is relatively high, it is not easy to be interfered by the appearance of the ear when measuring the body temperature. Further, when the temperature sensor is set corresponding to the position P2, there is sufficient space for integrating the components in the earphone without being affected by the sound components.

Figure 8:
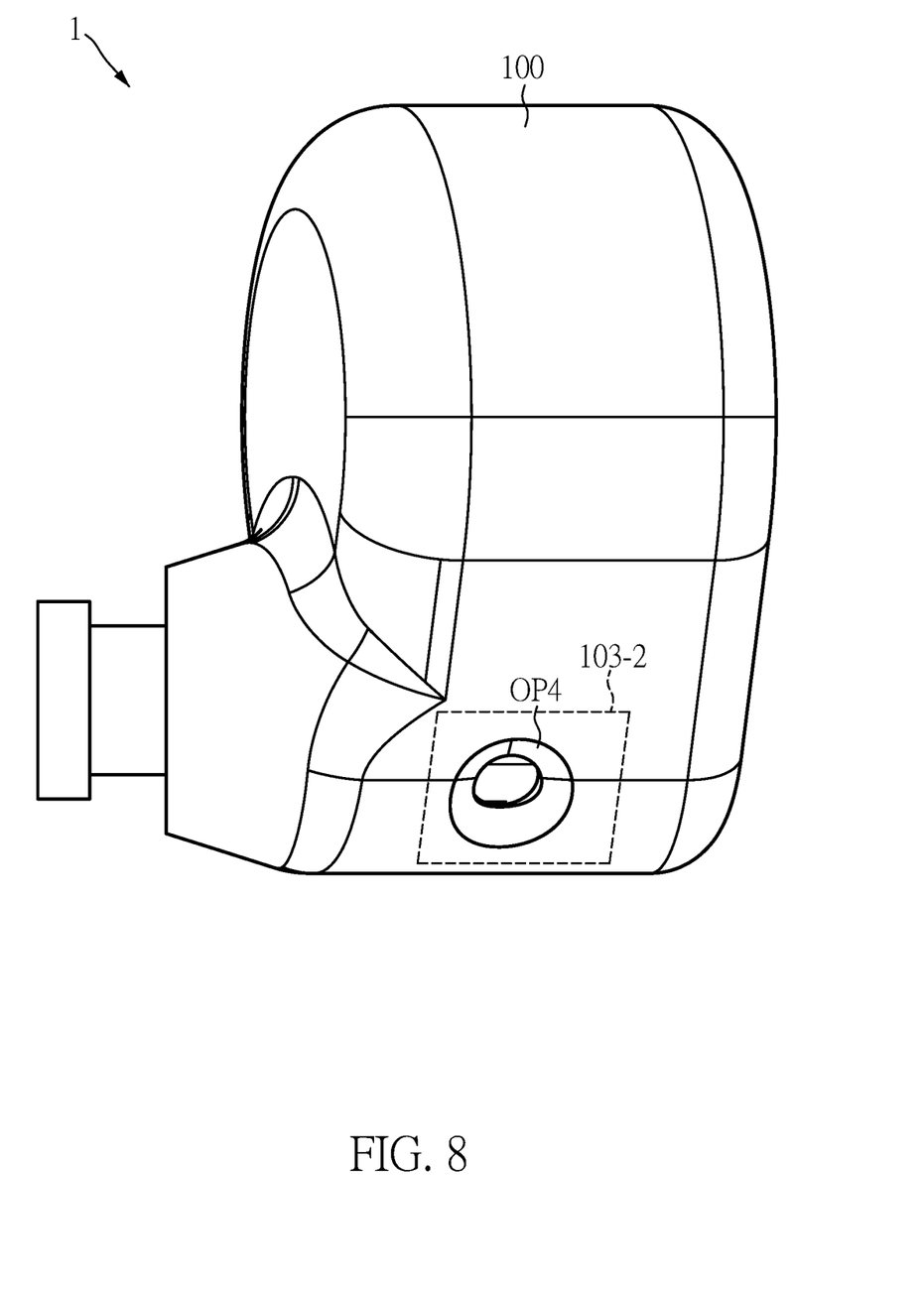
FIG. 8 shows yet another schematic side view of an earbud according to one embodiment of the present disclosure.

Referring to FIG. 8, FIG. 8 shows yet another schematic side view of an earbud according to one embodiment of the present disclosure. In the earbud 1 of FIG. 8, the housing 100 further defines a fourth opening OP4. In this case, the first temperature sensor 103 can be positioned to align the fourth opening OP4, or the earbud 1 can further include a third temperature sensor 103-2 positioned along the interior surface 101 of the housing 100 and aligned with the fourth opening OP4 for non-contact temperature sensing.

Figure 9A:
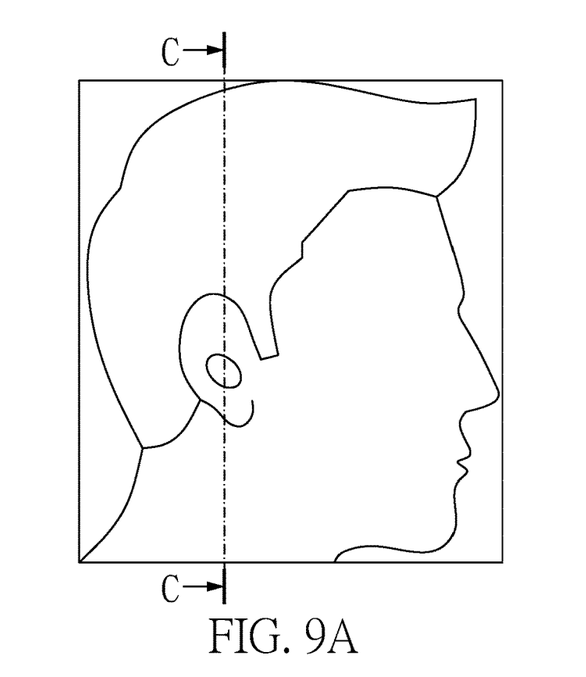
FIG. 9A is a schematic side view of a user wearing an earbud provided by the present disclosure.
Figure 9B:
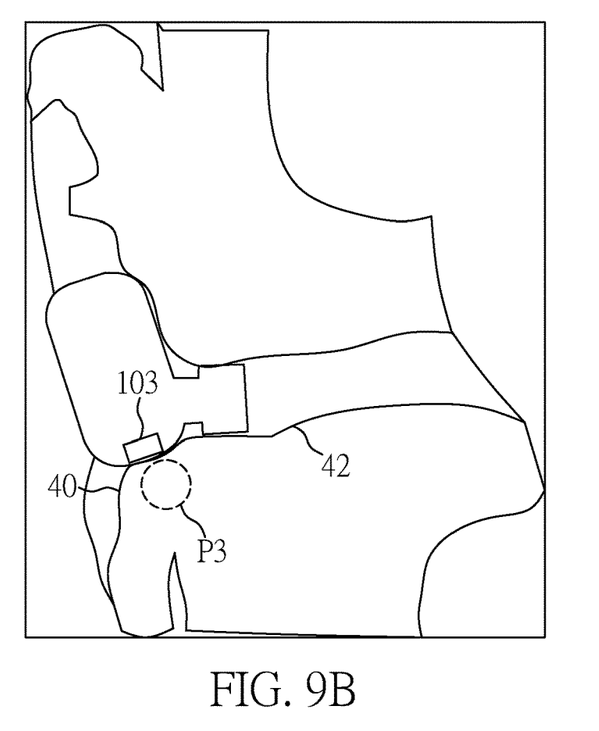
FIG. 9B is a schematic cross-sectional view taken along line C-C of FIG. 9A.

Reference can be further made to FIGS. 9A and 9B. FIG. 9A is a schematic side view of a user wearing an earbud provided by the present disclosure, and FIG. 9B is a schematic cross-sectional view taken along line C-C of FIG. 9A. As shown in FIG. 9B, when the earbud 1 being positioned for use within the ear of the user, the third opening OP4 aligns with an inner edge of the antitragus 40, such that the third temperature sensor 103-2 detects a body temperature from the inner edge of the antitragus 40 (i.e., the position P3) of the user through the fourth opening OP4. When measuring the body temperature through the position P3, due to the good airtightness of this position, the sensor data is not easily affected by the environment. In addition, when the temperature sensor is set corresponding to the position P3, there is sufficient space for integrating the components in the earphone without being affected by the sound components.

Figure 10:
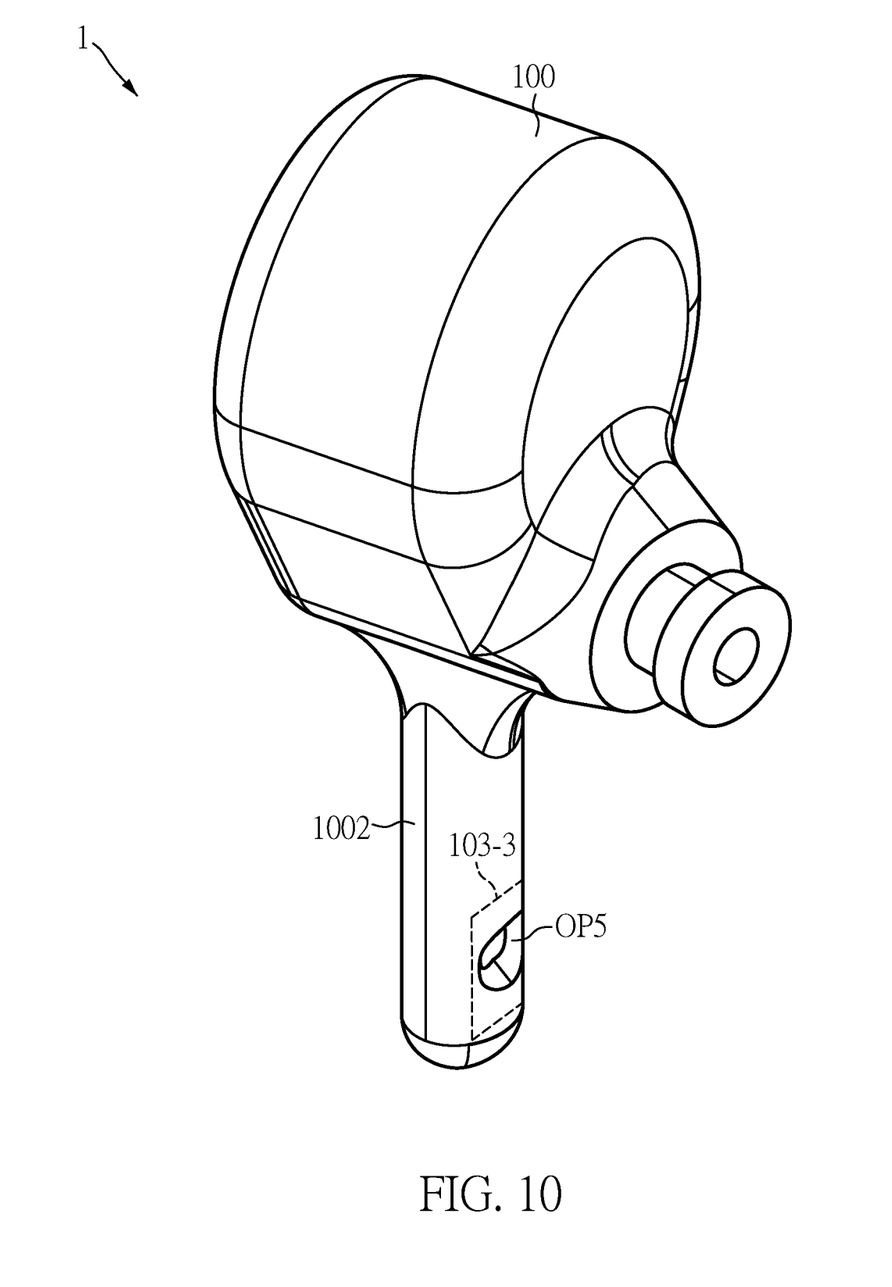
FIG. 10 shows yet another schematic side view of an earbud according to one embodiment of the present disclosure.

Referring to FIG. 10, FIG. 10 shows yet another schematic side view of an earbud according to one embodiment of the present disclosure. In the earbud 1 of FIG. 10, the housing further includes a second protrusion 1002 with the fifth opening OP5 at a distal end of the second protrusion 1002 that provides the fifth opening OP5 corresponding to the cheek close to the ear.

Therefore, in this case, the first temperature sensor 103 can be positioned to align the fifth opening OP5, or the earbud 1 can further include a fourth temperature sensor 103-3 positioned along the interior surface 101 of the housing 100 and aligned with the fourth opening OP5 for non-contact temperature sensing.

Figure 11A:
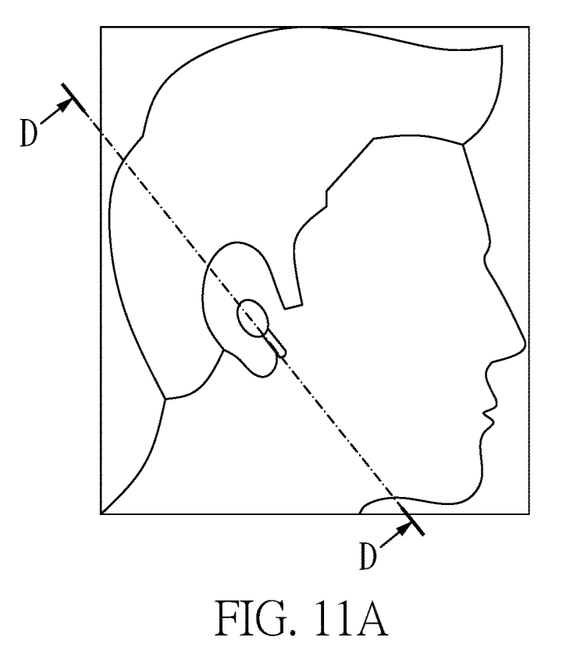
FIG. 11A is a schematic side view of a user wearing an earbud provided by the present disclosure.
Figure 11B:
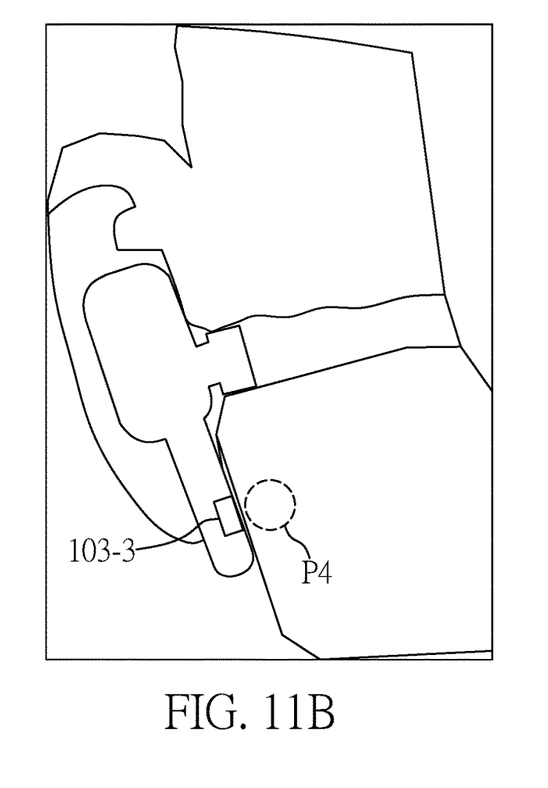
FIG. 11B is a schematic cross-sectional view taken along line D-D of FIG. 11A.

Reference can be further made to FIGS. 11A and 11B. FIG. 11A is a schematic side view of a user wearing an earbud provided by the present disclosure, and FIG. 11B is a schematic cross-sectional view taken along line D-D of FIG. 11A. As shown in FIG. 11B, when the earbud 1 being positioned for use within the ear of the user, the third opening OP4 aligns with the cheek close to the ear, such that the fourth temperature sensor 103-3 detects a body temperature from the cheek close to the ear (i.e., the position P4) of the user through the fifth opening OP5. When measuring the body temperature through the position P4, since the position P4 is close to the blood vessel, the body temperature can be estimated more accurately. Furthermore, since the appearance consistency of each person at this position is relatively high, it is not easy to be interfered by the appearance of the ear when measuring the body temperature. In addition, when the temperature sensor is set corresponding to the position P4, there is sufficient space for integrating the components in the earphone without being affected by the sound components.

It should be noted that one or more of the first temperature sensor 103, the second temperature sensor 103-1, the third temperature sensor 103-2, and the fourth temperature sensor 103-3 can be utilized to detect the body temperature of the user. When more than one sensor is used, the body temperature can be estimated more accurately since errors can be reduced by considering multiple sensor data.

Figure 12:
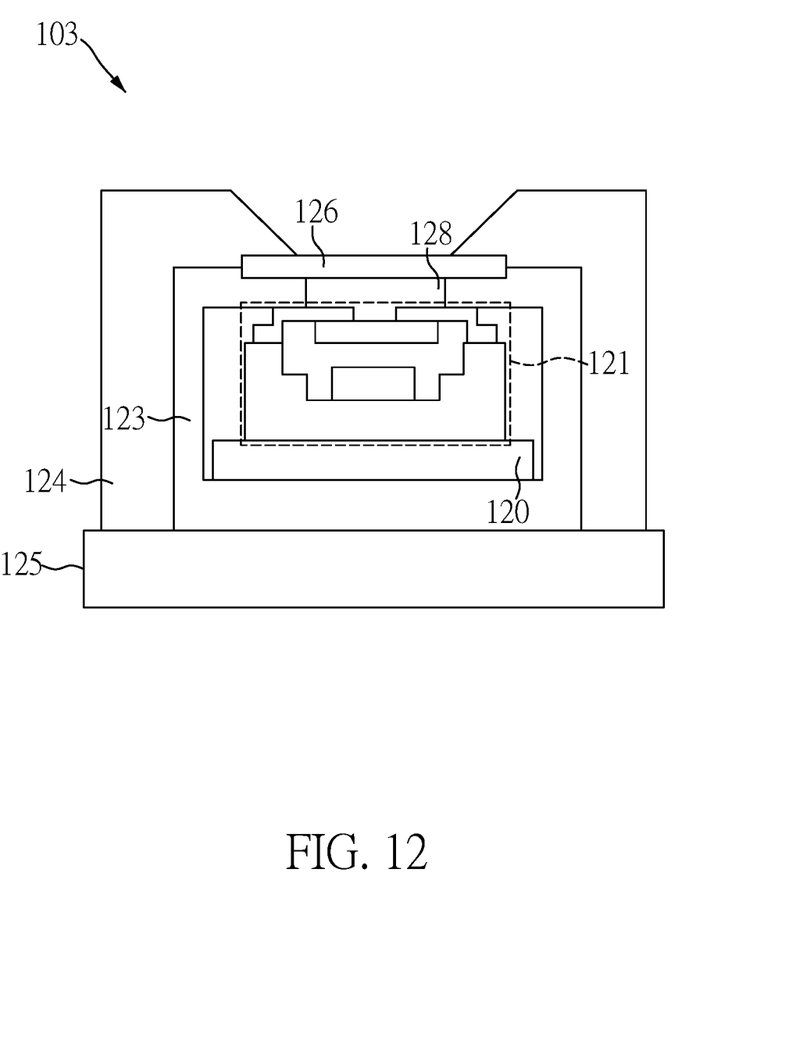
FIG. 12 is a cross-sectional view of a first temperature sensor according to one embodiment of the present disclosure.

Reference can be made to FIG. 12, which is a cross-sectional view of a first temperature sensor according to one embodiment of the present disclosure. As shown in FIG. 12, the first temperature sensor 103 can include a routing layer 120, a sensor chip 121, a cover filter 126, an internal housing 123 and an external housing 124. The sensor chip 121 is mounted on the routing layer 120, such as a flexible printed circuit board, and the sensor chip 121 can be, for example, a thermopile sensor chip used to detect body temperature by way of non-contact temperature sensing, but the present disclosure is not limited thereto.

Furthermore, the internal housing 123 can encapsulate the sensor chip 121 and the routing layer 120, and has a through via 128 corresponding to a sensing area of the sensor chip 121. The external housing 124 can encapsulate the internal housing on a thermal isolation layer 125, such as a thermal isolation tape.

The cover filter 126 can positioned between the internal housing 123 and the external housing 124, and align with the through via 128, and the cover filter 126 contacts with the internal housing 123. In certain embodiments, the internal housing 123 can be a metal housing, and the external housing 124 can be a plastic housing. Specifically, the thermal isolation layer 125, the internal housing 123 and the external housing 124 can be used to provide good thermal isolation for the temperature sensor.

Although the temperature sensing can be performed by utilizing the non-contact infrared sensors together with the openings in the embodiments of the present disclosure, in another embodiment, contact temperature sensing can also be utilized. For example, one or more temperature sensors each having a metal layer can be disposed at the positions corresponding to the first through fourth openings OP1-OP4 on the surface of the housing 100, such that when the skin of the user contacts the metal layer, the temperature sensor can then be used to sense a skin temperature of the user, but the present disclosure is not limited thereto.

BENEFICIAL EFFECTS OF THE EMBODIMENTS

In conclusion, in the earbud with temperature sensing provided by the present disclosure, one or more openings can be arranged to align with one or more of an inner side of the tragus close to the ear canal, the cavum conchae, an inner edge of the antitragus, or the cheek close to the ear, such that the temperature sensor can detect a body temperature of the user through the one or more openings with good airtightness and high accuracy, while reserving sufficient space for integrating the components in the earphone without being affected by the sound components.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An earbud with temperature sensing, comprising:
a housing defining a first opening, a second opening and a third opening;
a speaker disposed within the housing and oriented so that audio emitted by the speaker exits the housing through the first opening defined by the housing;
a first temperature sensor positioned along an interior surface of the housing and aligned with the second opening in the housing for non-contact temperature sensing;
a second temperature sensor positioned along the interior surface of the housing and aligned with the third opening in the housing for non-contact temperature sensing,
wherein, in response to the earbud being positioned for use within an ear of a user, the second opening aligns with one of an inner side of the tragus close to the ear canal, the cavum conchae, and an inner edge of the antitragus, and the third opening aligns with the cheek close to the ear, such that the first temperature sensor and the second temperature sensor detect a body temperature of the user through the second opening and the third opening, respectively, and the body temperature is estimated by considering sensor data of the first temperature sensor and the second temperature sensor.

2. The earbud according to claim 1, wherein the housing further includes a first protrusion with the first opening at a distal end of the first protrusion that provides the first opening through which the audio emitted by the speaker exits the housing.

3. The earbud according to claim 2, further comprising an ear cap pivotally coupled to the distal end of the first protrusion by a hinge.

4. The earbud according to claim 1, wherein the housing further includes a second protrusion with the second opening at a distal end of the second protrusion that provides the second opening corresponding to the cheek close to the ear.

5. The earbud according to claim 1, further comprising:
a processor disposed within the housing and configured to receive sensor data from the first temperature sensor, wherein the processor is configured to determine from the sensor data whether the earbud is inserted in the user's ear.

6. The earbud according to claim 5, further comprising:
a wireless transceiver disposed within the housing; and
an energy storage device disposed within the housing and providing power for operation of the earbud.

7. The earbud according to claim 1, further comprising:
a plurality of sensor positioning pins positioned along the interior surface of the housing and around the second opening in the housing, such that the first temperature sensor aligns with the second opening by engaging the plurality of sensor positioning pins.

8. The earbud according to claim 1, wherein the housing further defines a fourth opening, and the earbud further comprises:
a third temperature sensor positioned along the interior surface of the housing and aligned with the fourth opening in the housing for non-contact temperature sensing.

9. The earbud according to claim 8, wherein, in response to the earbud being positioned for use within an ear of a user, the second opening, the third opening and the fourth opening respectively align with three of the inner side of the tragus close to the ear canal, the cavum conchae, the inner edge of the antitragus, and the cheek close to the ear, such that the first temperature sensor, the second temperature sensor and the third temperature sensor detect the body temperature of the user through the second opening, the third opening and the fourth opening, respectively.

10. The earbud according to claim 1, wherein the housing further defines a fourth opening and a fifth opening, and includes a second protrusion with the fifth opening at a distal end of the second protrusion that provides the fifth opening corresponding to the cheek close to the ear, and the earbud further comprises:
a third temperature sensor positioned along the interior surface of the housing and aligned with the fourth opening in the housing for non-contact temperature sensing; and
a fourth temperature sensor positioned along the interior surface of the housing and aligned with the fifth opening in the housing for non-contact temperature sensing.

11. The earbud according to claim 10, wherein, in response to the earbud being positioned for use within an ear of a user, the second opening, the third opening, the fourth opening and the fifth opening respectively align with the inner side of the tragus close to the ear canal, the cavum conchae, the inner edge of the antitragus; and
wherein the first temperature sensor, the second temperature sensor, the third temperature sensor and the fourth temperature are configured to detect the body temperature of the user through the second opening, the third opening the fourth opening and the fifth opening, respectively.

12. The earbud according to claim 1, wherein the first temperature sensor includes:
a routing layer;
a sensor chip mounted on the routing layer;
an internal housing encapsulating the sensor chip and the routing layer, wherein the internal housing has a through via corresponding to a sensing area of the sensor chip; and
an external housing encapsulating the internal housing on a thermal isolation layer.

13. The earbud according to claim 12, wherein the first temperature sensor further includes a cover filter positioned between the internal housing and the external housing and aligned with the through via, and the cover filter contacts with the internal housing.

14. The earbud according to claim 12, wherein the internal housing is a metal housing, and the external housing is a plastic housing.

* * * * *